United States Patent
Puolakanaho et al.

(10) Patent No.: US 8,862,215 B2
(45) Date of Patent: Oct. 14, 2014

(54) RECONFIGURABLE SENSOR DEVICES MONITORING PHYSICAL EXERCISE

(71) Applicant: Polar Electro Oy, Kempele (FI)

(72) Inventors: Pertti Puolakanaho, Kiviniemi (FI); Elias Pekonen, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 13/742,812

(22) Filed: Jan. 16, 2013

(65) Prior Publication Data

US 2014/0200470 A1    Jul. 17, 2014

(51) Int. Cl.
*A61B 5/04*  (2006.01)
*A61B 5/00*  (2006.01)

(52) U.S. Cl.
CPC .................................... *A61B 5/0006* (2013.01)
USPC ............ 600/520; 600/544; 600/546; 324/649

(58) Field of Classification Search
None
See application file for complete search history.

(56) References Cited

U.S. PATENT DOCUMENTS

| | | | | |
|---|---|---|---|---|
| 5,598,849 | A | * | 2/1997 | Browne ......................... 600/520 |
| 5,921,891 | A | * | 7/1999 | Browne ............................. 482/8 |
| 7,020,701 | B1 | | 3/2006 | Gelvin et al. |
| 2004/0171464 | A1 | * | 9/2004 | Ashby et al. ..................... 482/54 |
| 2006/0020177 | A1 | * | 1/2006 | Seo et al. ....................... 600/300 |
| 2008/0252445 | A1 | | 10/2008 | Kolen |
| 2009/0063187 | A1 | | 3/2009 | Johnson |
| 2009/0269728 | A1 | * | 10/2009 | Verstegen et al. ............. 434/247 |
| 2010/0022882 | A1 | | 1/2010 | Duckworth |
| 2010/0179454 | A1 | | 7/2010 | Davies |
| 2011/0246509 | A1 | * | 10/2011 | Migita et al. .................. 707/769 |
| 2012/0220428 | A1 | | 8/2012 | Carlson |

OTHER PUBLICATIONS

European Search Report, Application No. EP 14150889, Apr. 15, 2014, 2 pages.

* cited by examiner

*Primary Examiner* — Brian T Gedeon
*Assistant Examiner* — Ankit Tejani
(74) *Attorney, Agent, or Firm* — Hoffmann & Baron, LLP

(57) ABSTRACT

The present document discloses an apparatus comprising at least one processor and at least one memory including a computer program code. The at least one memory and the computer program code are configured, with the at least one processor, to cause the apparatus to: trigger a start of a physical exercise; in response to said triggering, start a measurement mode in which the apparatus receives measurement data of the physical exercise wirelessly from at least one sensor device and analyzes the received measurement data; detect a predetermined event in the received measurement data during the physical exercise; and in response to detecting said predetermined event, cause transmission of a reconfiguration message to at least one of the at least one sensor device to reconfigure at least one parameter of said at least one of the at least one sensor device.

14 Claims, 4 Drawing Sheets

RECONFIGURABLE SENSOR DEVICES MONITORING PHYSICAL EXERCISE

BACKGROUND

1. Field

The invention relates to the field of biometric measurements and, particularly to sensor used for such measurements.

2. Description of the Related Art

Heart-rate monitors and other biometric sensors are commonly used by professional athletes as well as by conventional people practicing exercising. Heart-rate monitors and other biometric sensors typically provide a user with information enabling efficient workout. A typical heart-rate monitoring system includes a biometric sensor attached to the body of the user and configured to measure heart-rate of the user, to transmit the measured heart-rate to another device, e.g. a training computer. The other device receives the heart-rate information from the biometric sensor, processes the heart-rate information, and displays the processed heart-rate information. The other device may also process the heart-rate so as to calculate more advanced information, such as energy expenditure and fitness parameters of the user.

SUMMARY

According to an aspect of the present invention, there is provided an apparatus comprising at least one processor and at least one memory including a computer program code. The at least one memory and the computer program code are configured, with the at least one processor, to cause the apparatus to: trigger a start of a physical exercise; in response to said triggering, start a measurement mode in which the apparatus receives measurement data of the physical exercise wirelessly from at least one sensor device and analyses the received measurement data; detect a predetermined event in the received measurement data during the physical exercise; and in response to detecting said predetermined event, cause transmission of a reconfiguration message to at least one of the at least one sensor device to reconfigure at least one parameter of said at least one of the at least one sensor device.

According to another aspect of the present invention, there is provided an apparatus comprising at least one processor and at least one memory including a computer program code. The at least one memory and the computer program code are configured, with the at least one processor, to cause the apparatus to: trigger a start of a physical exercise; in response to said triggering, start a measurement mode in which the apparatus receives measurement data of the physical exercise wirelessly from at least one sensor device and analyses the received measurement data; detect a change of a sports type from the received measurement data during the physical exercise; and in response to detecting said change of the sports type, determine a new sports type from the received measurement data and a new set of sensors associated with the new sports type and cause transmission of a reconfiguration message to the at least one of the at least one sensor devices to change to the new set of sensors.

According to another aspect of the present invention, there is provided an apparatus comprising at least one processor and at least one memory including a computer program code. The at least one memory and the computer program code are configured, with the at least one processor, to cause the apparatus to: trigger a start of a physical exercise; in response to said triggering, start a measurement mode in which the apparatus receives heart rate measurement data of the physical exercise wirelessly from at least one heart rate sensor and analyses the received heart rate measurement data; detect a predetermined event in the heart rate measurement data; reconfigure the at least one heart rate sensor to carry out at least one of the following in response to the detected predetermined event in the heart rate measurement data: change a wireless transmission mode of the heart rate measurement data, change a data storage mode of the heart rate measurement data in the at least one heart rate sensor.

Further embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
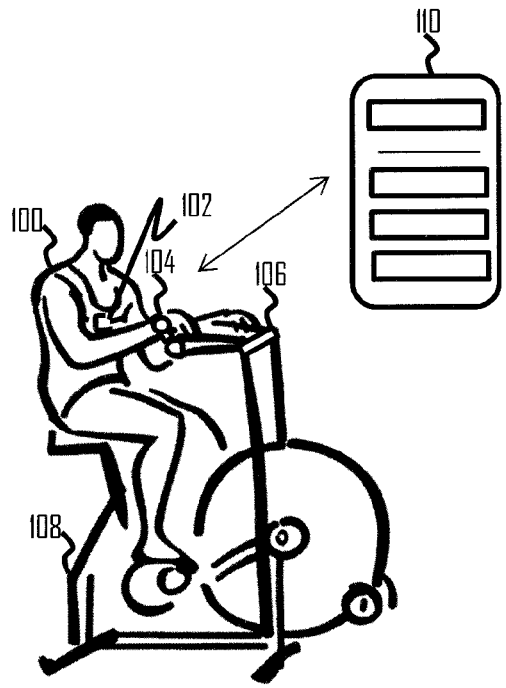
FIG. 1 illustrates a system for measuring and processing exercise-related measurement data.

FIG. 1 illustrates an exemplary system for use to measure exercise-related data in order to monitor a physical exercise performed by a user 100. Referring to FIG. 1, the user 100 may have various sensor devices 102 that measure and process the exercise-related data. The user 100 is provided with the following equipment: a user interface apparatus in the form of a wrist unit 104, a portable training computer 110, or a training computer 106 comprised in a gym apparatus 108. In an embodiment applicable to team sports, the user interface device apparatus 104, 106, 110 may be carried by a coach or a person other than an athlete carrying the sensor device(s). The sensor devices used by the user 100 during the physical exercise may comprise a heart rate sensor 102 worn on the chest of the user 100, an upper-arm-mounted positioning device, a shoe-mounted stride sensor, a bike sensor configured to measure the speed of a bike, a cycling cadence, and/or a pedaling power of the user and a swimming sensor configured to monitor swimming motions, water pressure etc. The sensor device may further comprise other motion sensor, e.g. one or more accelerometers, a gyroscope, and/or a magnetometer. The sensor devices may communicate wirelessly with the user interface device(s) 104, 106, 110. Various sensor devices may be flexibly used as needed, i.e. all of them are not necessarily needed all the time, or by all users, or in all use cases, as described below.

The user interface apparatus 104, 106, 110 comprises a user interface which may comprise a display, a loudspeaker, a keyboard, and/or a keypad. The display may be a liquid crystal display, for example, but it may also be implemented by any appropriate technique. The display may also incorporate other user interaction components, such as touch input, or haptic feedback, i.e. the display may be a touch screen. The keyboard/keypad may comprise a complete (QWERTY) keyboard, a mere numeric keypad or only a few push buttons and/or rotary buttons. In addition, the user interface may comprise other commonly used user interface elements, for example a device for focusing a cursor (mouse, track ball, various arrow keys, touch sensitive area etc.) or elements enabling audio control. A parameter relating to the exercise may be shown on the user interface, e.g. on the display. The user interface device may also comprise a communication circuitry configured to communicate with the sensor devices 102, as described in greater detail below.

The heart rate sensor 102 is used for measuring the user's heart activity. The heart activity comprises heart rate and one or multichannel ECG (Electrocardiogram), for example. The heart activity sensor 102 may further measure other physiological parameters that can be measured from the user. There exist various wireless heart rate monitoring concepts where a heart rate sensor attached to the user's chest measures the user's heart activity and transmits associated heart activity data telemetrically to a heart rate receiver, such as the wrist unit 104 attached to the user's wrist. The transmission of the heart activity data may utilize the principles of time division and/or packet transmission, for example. However, the heart-rate (and/or other biometric data) is conventionally only measured, and the measurement data is forwarded to the user interface device 104, 106, 110 for further processing.

The positioning device receives external location information. The positioning device may be a receiver of a global navigation satellite system. Such a system may be the Global Positioning System (GPS), the Global Navigation Satellite System (GLONASS), the Galileo Positioning System (Galileo), the Beidou Navigation System, or the Indian Regional Navigational Satellite System (IRNSS), for example. The positioning device determines its location elements, such as longitude, latitude, and altitude, using signals transmitted from satellites orbiting the earth. Besides global navigation satellites, the positioning device may also determine its location by utilizing other known positioning techniques. It is well known that by receiving radio signals from several different base stations, a mobile phone may determine its location. The positioning device may utilize such schemes as well. In an embodiment of the invention, the positioning device applies proprietary positioning methods based on optical or electromagnetic measurements.

The stride sensor (or the swimming sensor) comprises one or more motion sensors measuring the movement of the user, a processing unit configured to process the measured motion data of the user and to transmit the processed data to the user interface device 104, 106, 110 over a wireless connection. The motion sensor actually measures its own motion based on acceleration measurement, for example, and converts the acceleration into an electric signal. The electric signal is converted into a digital format in an AD converter. Acceleration can be expressed by the unit of measurement g. One g is the acceleration caused to an object by earth's gravity. Accelerations between −2 and +2 g can usually be measured from human movement. Various techniques may be used for measuring acceleration. Piezo-resistor technology employs material whose resistance changes as it compresses. The acceleration of mass produces a force in a piezo resistor. If a constant current is supplied through the piezo resistor, its voltage changes according to the compression caused by acceleration. In piezo-electric technology, a piezo-electric sensor generates charging when the sensor is accelerated. In silicon bridge technology, a silicon chip is etched so that a silicon mass remains on it at the end of a silicon beam. If acceleration is directed to the silicon chip, the silicon mass focuses a force on the silicon beam, thus changing the resistance of the silicon beam. Micro-machined silicon technology is based on the use of a differential capacitor. Voice coil technology is based on the same principle as a microphone. Examples of suitable movement sensors include: Analog Devices ADXL105, Pewatron HW or VTI Technologies SCA series. The implementation of the motion sensor may also be based on other appropriate techniques, for example on a gyroscope integrated into a silicon chip or on a micro vibration switch incorporated into a surface mounting component. A magnetometer may also be considered as an embodiment of the motion sensor.

In summary, the sensor devices each comprise at least one measurement sensor which measures some aspect of the exercise. The sensor devices may provide raw measurement data without further processing, as a conventional heart activity sensor does, or the sensor devices may process the raw data before outputting it. An embodiment of the sensor device comprises a plurality of sensors measuring different parameters of the physical exercise. The sensor device may thus comprise two or more of the following sensors or sensor circuitries in any combination: the heart rate sensor, the stride sensor, the motion sensor, the positioning sensor, the swimming sensor, the cycling cadence sensor, and the cycling power sensor.

In an embodiment, the sensor device 102 device comprises an accelerometer and at least one of the following: A GPS sensor, an gyroscope, a magnetometer, a heart rate sensor. In an embodiment, the accelerometer and at least one of the GPS sensor, the gyroscope, the magnetometer and the heart rate sensor are comprised by the same casing structure. In an embodiment, the sensor comprises attachment means, such as press studs for attaching the sensor mechanical to a chest strap. The attachment means may comprise electric connection capability for connecting the sensor to the sensor electrically to the chest strap. In such a case, the chest strap may comprise ECG skin electrodes. In an embodiment, the sensor device 102 is integrated as a part of the chest strap comprising permanent electromechanical attachment to the chest strap.

In an embodiment of the invention, the reconfiguration message comprises instructions to start streaming acceleration data to the user interface device 104, 106, 108.

In an embodiment of the invention, the reconfiguration message comprises instructions to stop streaming acceleration data to the user interface device 104, 106, 108.

In an embodiment of the invention, the reconfiguration message comprises instructions to start streaming gyroscopic data to the user interface device 104, 106, 108.

In an embodiment of the invention, the reconfiguration message comprises instructions to stop streaming gyroscopic data to the user interface device 104, 106, 108.

In an embodiment of the invention, the reconfiguration message comprises instructions to start streaming location data to the user interface device 104, 106, 108.

In an embodiment of the invention, the reconfiguration message comprises instructions to stop streaming location data to the user interface device 104, 106, 108.

In an embodiment of the invention, the reconfiguration message comprises instructions to start streaming magnetometer data to the user interface device 104, 106, 108.

In an embodiment of the invention, the reconfiguration message comprises instructions to stop streaming magnetometer data to the user interface device 104, 106, 108.

In an embodiment of the invention, the reconfiguration message comprises instructions to start streaming ECG data to the user interface device 104, 106, 108.

In an embodiment of the invention, the reconfiguration message comprises instructions to stop streaming ECG data to the user interface device 104, 106, 108.

In embodiment of the invention, the user interface device 104, 106, 108 is configured to receive streamed data and store the streamed data into memory.

In embodiment of the invention, the user interface device 104, 106, 108 is configured to receive streamed data and store the streamed data into memory. In an embodiment, the processor 10 of the user interface device 104, 106, 108 is configured to run a computer process on the stored data.

In embodiment of the invention, the user interface device 104, 106, 108 is configured to receive streamed data and run a computer process on the streamed data during streaming.

In an embodiment of the invention, the computer process implements a gait analysis based on at least acceleration data. The gait analysis includes at least one of the following: determination of a time period between two signatures in the acceleration signal, calculation of the first integral with respect of time of the acceleration signal, calculation of the second integral with respect of time of the acceleration signal, determination of maximum value of acceleration from the acceleration signal, determination of angular measure from at least two spatial components of the acceleration signal, determination of direction of gravity from the acceleration signal, determination of step cadence from the acceleration signal, determination of propagation speed of the person from the acceleration signal, determination of mechanical impact on the person's body.

In embodiment, the gait analysis is further based on at least one of the following: gyroscopic data, magnetometer data, GPS data.

In an embodiment of the invention, the computer process implements an ECG analysis based on the ECG data. The ECG analysis comprises at least one of the following: Determination of amplitude of an ECG signal, determination of spectral content of the ECG data.

An embodiment of the present invention provides a sensor device 102 comprising an exercise-measurement circuitry configured to measure exercise-related measurement data related to the user 100 carrying out a physical exercise, a communication circuitry configured to provide the sensor device with bidirectional wireless communication capability with the user interface device 104, 106, 110, a processing circuitry, and a memory. The exercise-related measurement data is measurement data characterizing an exercise, and embodiments of the measurement data may comprise heart rate measurement data, motion measurement data, power measurement data, positioning measurement data cadence measurement data, and/or ambient measurement data. The ambient measurement data may comprise measurement data characterizing environmental conditions such as time, weather, temperature, humidity, and air/water pressure.

Providing a bidirectional communication link between the sensor device 102 and the user interface device 104, 106, 110 enables input of configuration data into the sensor device 102 carrying out the measurement. The bidirectional wireless communication link may be realized according to the specifications of Bluetooth (or Bluetooth low energy), wireless USB (Universal Serial Bus), Zigbee or IEEE 802.15.4, or wireless local area network (IEEE 802.11x, WiFi).

Figure 2:
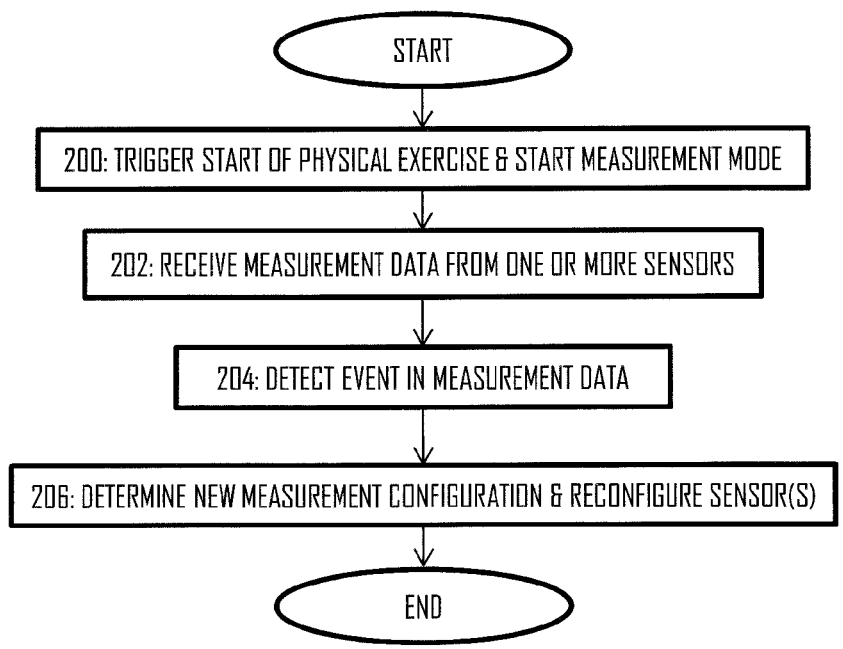
FIGS. 2 and 3 are flow diagrams of processes for configuring sensor devices according to some embodiments of the invention.

FIG. 2 illustrates a flow diagram of a process according to an embodiment of the invention. The process may be carried out in the user interface device 104, 106, 110. Referring to FIG. 2, the user interface device 104, 106, 110 triggers a start of a physical exercise in the user interface device in block 200. The triggering may be based on a user input provided by the user 100 of the user interface device 104, 106, 110. In response to said triggering, the user interface device 104, 106, 110 starts a measurement mode in the user interface device 104, 106, 110 in block 202. The user interface device 104, 106, 110 receives measurement data of the physical exercise wirelessly from at least one sensor device 102 and analyses the received measurement data in the measurement mode. In block 204, the user interface device 104, 106, 110 detects a predetermined event in the received measurement data during the physical exercise. In response to detecting said predetermined event in block 204, the user interface device 104, 106, 110 transmits a reconfiguration message to at least one of the at least one sensor device 102, wherein the reconfiguration message changes an active set of sensors for the physical exercise.

In an embodiment, the reconfiguration message changes at least one operational parameter of the sensor device 102 during the physical exercise. The changed operational parameters may comprise the change of the active set of sensors in the above-described manner, or it may comprise a change in processing measurement signals, and/or a change in transmission of the measurement data from the sensor device to the user interface device 104, 106, 108, for example.

Figure 3:
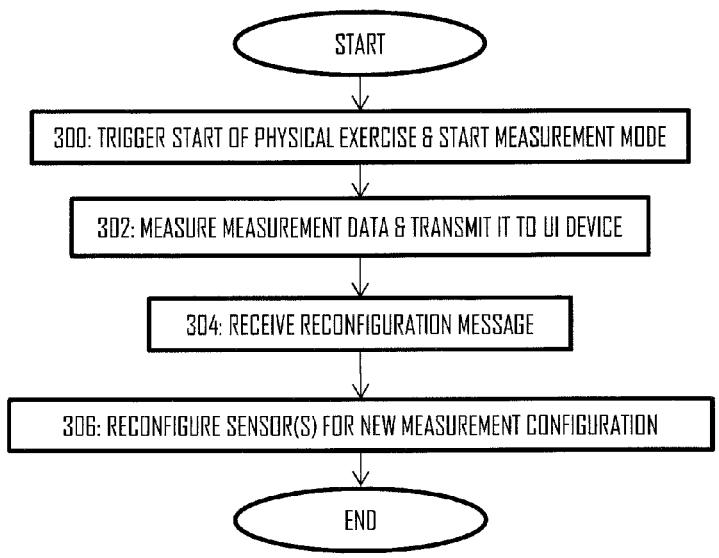
Figure 4:
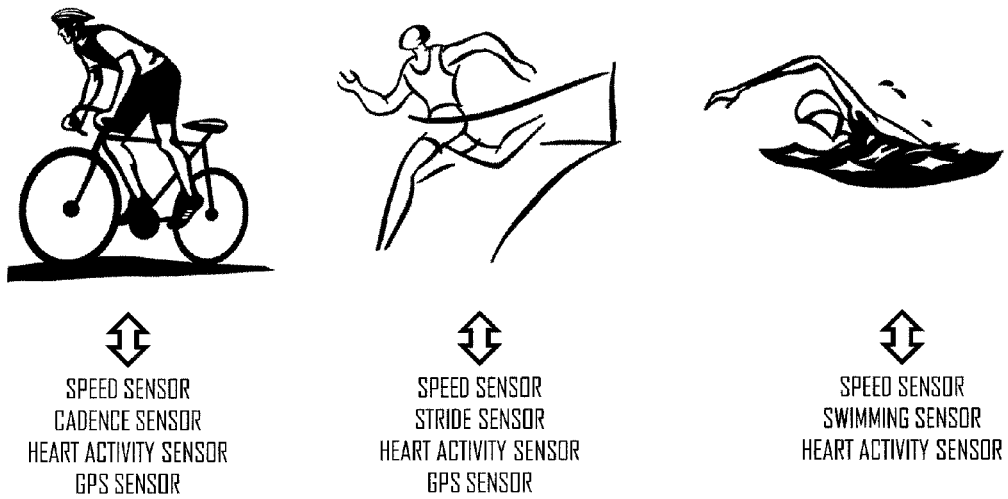
FIG. 4 illustrates association between different sports types and associated active sets of sensors.

FIG. 3 illustrates a corresponding operation in the sensor device 102. Referring to FIG. 3, the start of a physical exercise is triggered in the sensor device 102 in block 300. The triggering mechanism may be an activation signal received from the user interface device 104, 106, 110. In response to said triggering, the sensor device 102 starts a measurement mode in the sensor device 102. In the measurement mode, the sensor device 102 measures measurement data of the physical exercise and transmits the measurement data wirelessly to the user interface device 104, 106, 110 in block 302. In response to the above-mentioned detection of the predetermined event in the measurement data in the user interface device 104, 106, 110, the sensor device receives the reconfiguration message wirelessly from the user interface device 104, 106, 110 in block 304. The reconfiguration message comprises a measurement configuration for the physical exercise. In response to the reception of the new measurement configuration defined by the reconfiguration message, the sensor device 102 changes an active set of sensors employed to carry out the measurements for the physical exercise (block 306).

In an embodiment, the predetermined event detected in the measurement data is a change of a sports type. The user interface device 104, 106, 110 may detect the change of the sports type from motion measurement data, positioning measurement data, and/or time measurement data, for example. The user interface device 104, 106, 110 may store reference motion data for a plurality of different sports types, and the detection of the sports type may be realized by comparing received motion measurement data with the reference motion data of different sports types. The sports type represented by the reference data providing the highest correlation with the received motion measurement data may be determined to be the sports type the user 100 is currently practicing. In another embodiment, the change of the sports type is detected from the time measurements and a predetermined training program for the physical exercise. The training program may comprise separate time slots for a plurality of different sports types, and the user interface device may determine the change of the sports type when a time slot of one sports type ends and a time slot of another sports type starts. The time may be measured by a clock or, in general, any sensor capable of measuring time. In yet another embodiment, the change of the sports type is detected from the positioning measurement data and the predetermined training program. The training program may specify location coordinates where the sports type is to change from one sports type to another. The training program may also specify the sports types that start and end at the specified location. Accordingly, the user interface device may determine from location measurements when the user 100 is in a location where the sports type changes. It should be appreciated that other measurement data may be used to determine the new sports type, e.g. pressure sensor may be used to determine when the sensor device is at least partially submerged and, thus, determine that the current sports type is swimming.

In one use case where the predetermined event is the change of the sports type, the user interface device 104, 106, 110 detects the sports type based on a GPS sensor in triathlon. The sports type is expected to change from swimming to cycling at a determined location. Upon entering the determined location, as indicated by the GPS sensor, the user interface device 104, 106, 110 transmits the reconfiguration message to a cycling sensor device and to a chest sensor device 102 equipped with a heart rate sensor and a motion sensor. The chest sensor device 102 may deactivate the motion sensor in response to the reception of the reconfiguration message, and the cycling sensor device may activate a cycling cadence sensor and/or a cycling power sensor. As a consequence, the motion sensor of the chest sensor device no longer sends the motion measurement data to the user interface device 104, 106, 110, while the sensors of the cycling sensor device start to transmit their measurement data to the user interface device 104, 106, 110.

FIG. 3 illustrates examples of different sports types and embodiments of active sets of sensors that may be associated with each sports type. With respect to the cycling as the sports type, the active set of sensors may comprise at least one of the following sensors: the speed sensor, the cycling cadence sensor, the cycling power sensor, the heart rate or heart activity sensor, the positioning sensor. With respect to the running as the sports type, the active set of sensors may comprise at least one of the following sensors: the speed sensor, the stride sensor, the heart rate or heart activity sensor, the positioning sensor. With respect to the swimming as the sports type, the active set of sensors may comprise at least one of the following sensors: the speed sensor, the swimming sensor, the heart rate or heart activity sensor, the positioning sensor.

In the context of the present description, the sensor may be interpreted broadly such that the same physical sensor may operate as a plurality of different sports-type-specific sensors. The change of the active set of sensors as carried out by the user interface device and the reconfiguration message may activate or disable the physical sensor, or it may maintain the sensor operational but change the sensor functionality in terms of applied sports type. In an embodiment where the physical sensor is a motion sensor, the reconfiguration message may change the functionality of the motion sensor from a stride sensor into a swimming sensor when the sports type changes from the running to swimming (and vice versa). In practice, the reconfiguration message may change a motion sensing algorithm used by a processor of the sensor device. According to this aspect, the change of the active set of sensor may, in some scenarios, comprise maintaining the same set of physical sensors but changing the function to measure a feature of a new sports type, e.g. change from measuring running motion to measuring swimming motion. Changing the function may comprise changing detection logic of the sensor. The detection logic may comprise applied thresholds, e.g. one or more thresholds used to detect a QRS complex in a heart rate signal, one or more thresholds used to detect a stride from acceleration measurement data, measurement signal signature thresholds used to identify the measurement signal, correlation parameters used to identify the measurement signal (e.g. selection of reference signal(s), parameters of the reference signal), averaging time window, etc.

According to another aspect, the sensor may be interpreted to encompass a physical sensor circuitry dedicated to a certain sports type, and the reconfiguration message may only activate or disable the physical sensor circuitry when the sports type changes. According to this aspect, the change of the active set of sensor may always change the active set of physical circuitries.

In another embodiment, the predetermined event is inaccuracy in the measurement data. For example, when the measurement data is detected to be inaccurate, the user interface device may activate an additional sensor to improve the accuracy. On the other hand, if the accuracy is found to be sufficiently accurate, the user interface device may deactivate at least one sensor in order to reduce power consumption. A gyroscope is a power-consuming unit, and the user interface device may optimize its utilization in terms of power consumption. The gyroscope may be used to improve the positioning accuracy, for example. Accordingly, when the user interface device detects inaccuracy, e.g. variance, volatility, etc. that exceeds a threshold level in the positioning measurement data provided by the positioning sensor, the user interface device may instruct the gyroscope to activate and start inertial measurements to improve the positioning accuracy. On the other hand, when the positioning measurement data provided by the positioning sensor shows reliable accuracy once again, the user interface device may instruct the gyroscope to deactivate and save power.

In another embodiment, the predetermined event is when a value or values of the measurement exceed a certain threshold level or fall below a certain threshold level. For example, when the user's heart rate or motion/acceleration increases above a certain threshold level, the user interface device may activate a new sensor (e.g. the gyroscope) to improve the measurement accuracy. When the measurement data falls below the threshold level, the new sensor may be deactivated.

Figure 5:
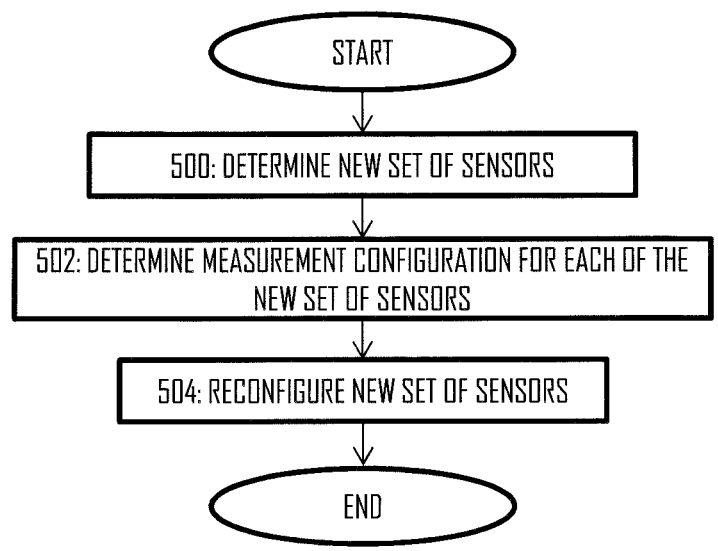
FIG. 5 is a detailed flow diagram of a process for determining measurement configuration for an active set of sensors according to an embodiment of the invention.

FIG. 5 illustrates an embodiment of block 206. Upon detecting the predetermined event in the measurement data, the user interface device 104, 106, 110 may determine a new set of sensors that comply with the detected event, e.g. the new sports type (block 500). In block 502, the user interface device determines a new measurement configuration for each sensor of the new set of sensors determined in block 500, and reconfigures the sensors by signaling the measurement configuration in the reconfiguration message (block 504). Table 1 below shows a list of embodiments of different events that may be detected, measurement configuration parameters that may be affected by the event detection, and how the sensor responds to the change of the measurement configuration. The measurement configuration parameters (middle column in Table 1) may comprise the contents of the reconfiguration message transmitted from the user interface device to the sensor device(s).

TABLE 1

| Event detection | Configuration parameters | Sensor response |
|---|---|---|
| Sports type | Predetermined index of new sports type | Change algorithm from a group of algorithms |
| | Algorithm parameters | Change of algorithm parameters |
| | Sampling rate | Change of sampling rate |
| | User interface index | Change of wireless output protocol |
| | Predetermined index for a communication protocol | Change sensor user interface functionality |
| | | Change of used component configuration |
| Phase within a sports type | Predetermined index representing an algorithm | Change algorithm from a group of algorithms |
| | Algorithm parameters | Change of algorithm parameters |
| | | Change of sampling rate |
| | | Change of wireless output protocol |
| | | Change sensor user interface functionality |
| | | Change of used component configuration |
| Heart rate event | Start/Stop command to store data | Start/stop storing data into memory (ECG, motion data) |
| | Command to stream data to the UI device | Start/stop streaming data |
| | Predetermined index for a communication protocol and/or security level | Mark start or stop point of data to be stored permanently |
| | | Transmit ECG data to the UI device |
| | | Change of communication protocol |
| | | Change of security level |
| Activity event(accelerometer) | Start/Stop command | Start/stop cardiac measurement |
| | GPS averaging time | Change GPS averaging |
| | Motion sensing sensitivity parameter | Change axis sensitivity (x, y, z) |
| | Sleep mode command | On/Off wrist unit sleep mode |
| Respiration event | Start/Stop command to store data | Start/Stop a respiration algorithm |
| | | Start/stop storing data |
| Energy expenditure event | Command to change an algorithm | Change to high altitude mode |
| | | Change to low temperature mode |

Upon detecting a new sports type, the user interface device may determine the new sports type, an index associated with the new sports type, and transmit the index to the sensor devices. The sensor devices may thus acquire knowledge of the new sports type and map the received index internally to a new measurement configuration. Accordingly, the sensor device may change the set of active sensors, select an algorithm from a group of algorithms for each active sensor according to the specified sports type, change algorithm parameters such as those listed above, change a sampling rate of a measurement signal, change a wireless communication protocol employed between the sensor device and the user interface device, change sensor device's user interface functionality (e.g. function behind a button or a display element of the sensor device), change used component configuration (e.g. change the active set of sensors in the sensor device). The change of the wireless communication protocol may comprise selecting a sports-type-specific protocol from a plurality of protocols supported by the sensor device and the user interface device, and/or selecting between a data streaming mode and a data storing mode. In the data streaming mode, the sensor device may stream the measurement data to the user interface device, as new measurement data is acquired while, in the data storage mode the sensor device may buffer the measurement data and transmit the measurement data in a bundle at the end of the physical exercise or upon request from the user interface device, for example.

In an embodiment, the reconfiguration message defines a change in a data transmission mode, and the sensor device may change the procedure in which the measurement data is transmitted to the user interface device in response to the received reconfiguration message.

In an embodiment, the reconfiguration message defines a change in a data storage mode, and the sensor device may change the procedure in which the measurement data is stored in a memory of the sensor device in response to the received reconfiguration message.

In an embodiment, the predetermined event is detection of a change of a phase within a sports type during the physical exercise. For example in interval type of training, the training comprises high intensity and low intensity phases, so the change of the phase may be a change in the intensity of the physical exercise. The change of the phase may be based on detecting that values of the measurement data exceed or fall below a determined threshold, e.g. an intensity threshold. The user interface device may employ different sensors for different phases of the exercise of the same sports type. For example, when a user interface device detects a sprint phase in cycling, it may activate a cycling power sensor to measure instantaneous powers the user applies to pedals and/or cranks of the cycle. The user interface unit may send to the cycling power sensor a reconfiguration message instructing the cycling power sensor to start storing power sampling points to the memory. The cycling power sensor thus starts storing the measurement data. Once the speed change is stopped, the user interface device may send a command to stop storing the measurement data and to transmit the measurement data to the user interface unit. During a constant, low-intensity cycling phase, the cycling power sensor may be deactivated, and the user interface device may use a cycling cadence sensor.

In an embodiment, the predetermined event is detection of a cardiac event in heart rate measurement data. The user interface device may detect a cardiac event in the heart rate measurement data by detecting at least one of the following: a heart rate threshold is exceeded, e.g. an upper or lower limit of the heart rate, RR intervals or heart rate variability; and a rhythmic pattern in the heart beats is detected, wherein the rhythmic pattern may indicate cardiac dysrhythmia. In response to the detection of the cardiac event, the user interface device may send a reconfiguration message to the heart rate sensor. The reconfiguration message may instruct the heart rate sensor to: start/stop storing ECG samples into memory; increase sampling interval for a given period of ECG measurement; detect certain patterns in the heart rate measurement signals, e.g. P-T waves. Accordingly, the user interface device may instruct the heart rate sensor to change the digital detection algorithm on the basis of the detected cardiac event.

In an embodiment, the predetermined event is a communication event, e.g. a radio sensor may detect presence of multiple sensor of the same type, e.g. sensors of with different users. The user interface device may thus determine the security level of the communication connection between the user interface device and the at least one sensor device on the basis of the communication event. The security level may be increased in proportion to the number of detected sensor devices.

As described above, the user interface device may detect the predetermined in the measurement data provided by one sensor or sensor device and, as a result, change the measurement configuration of another sensor or sensor device. The predetermined event may occur in the ambient conditions, e.g. it may be a temperature or humidity event, which triggers a change in the measurement configuration of a sensor measuring the user.

Figure 6:
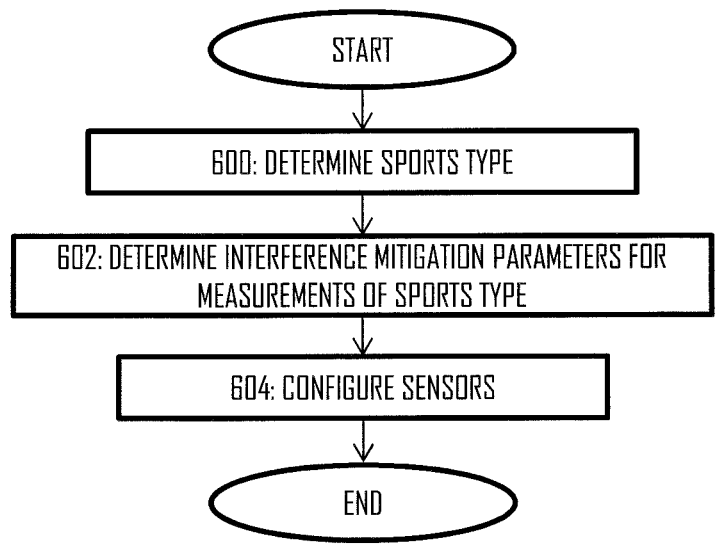
FIG. 6 is a flow diagram of a process for determining interference mitigation parameters for a sensor device according to an embodiment of the invention.

Another aspect of the invention relates to mitigating interference associated with measurements of different sports types. FIG. 6 illustrates an embodiment of the procedure for mitigating or avoiding interference during the measurements. The procedure may be carried out in a sensor device or in the user interface device, and it may be readily applied to the above-described embodiments. The mitigation may be based on determining the sports type. Referring to FIG. 6, the current sports type is determined in block 600. The determination may be based on a user input, wherein the user selects the sports type, or it may be based on automatic detection of the sports type from the measurement data, e.g. motion measurement data. In block 602, interference mitigation parameters may be determined for a measurement configuration of the determined sports type. Different interference mitigation parameters may be used for different sports types. In block 604, the at least one sensor is configured to apply the determined interference mitigation parameters.

The interference mitigation parameters may comprise selection of a measurement frequency band, one or more detection thresholds, and/or timing of measurements. For example, interference caused by high acceleration of stride impacts in running degrades the performance of heart rate measurements. The determination of the interference mitigation parameters may comprise selecting a measurement frequency band for the heart rate measurements outside the frequency range of the stride impacts. The frequency range of the stride impacts may be known beforehand or it may be measured from the acceleration data. The determination of the interference mitigation parameters may comprise selecting an upper limit for a heart rate detection threshold such that when the signal exceeds the upper limit, the impulse is not interpreted as a QRS complex. Accordingly, the stride impact may be eliminated. In connection with cycling, interference may be caused by an electric field caused by the motion (flutter) of a shirt in the wind. This interference typically resides on a higher frequency band than the QRS complex, so appropriate selection of the measurement frequency band eliminates this interference type. In gym training, interference to the heart rate measurements may be caused by electromyographic (EMG) signal caused by muscle contraction. This interference is temporary and typically located on a higher frequency band than the QRS complex, so appropriate selection of the measurement frequency band eliminates this interference type. Additionally, the heart rate detection logic may comprise an additional algorithm tracking the EMG and eliminating from the heart rate measurements those heart rate pulses during which high EMG interference is detected. In swimming, interference is caused by high amplitude variation caused by the water short-circuiting the sensor. This interference type may be mitigated by applying an adaptive gain control adapted to follow the short-circuiting caused by the water.

In an embodiment where the procedure is carried out in the user interface device, the user interface device may determine the sports type in the above-described manner and indicate the sports type to the sensor device according to the embodiments of the invention by transmitting the reconfiguration message. The reconfiguration message may comprise an index of the determined sports type, or it may comprise the determined interference mitigation parameters, e.g. the bandwidth and/or the timing of suspending the heart rate measurements. The user interface device may determine the frequency of the stride impacts, for example, from the motion measurements received from the stride sensor and configure the heart rate sensor to suspend the heart rate measurements for a duration and with a periodicity determined from the motion measurements. The user interface device may determine the frequency band of the interference from the received measurement data and configure the heart rate sensor to operate on a non-overlapping frequency band.

In the embodiment where the procedure of FIG. 6 is carried out in the sensor device, the sensor device may receive the measurement data required for determining the sports type and the interference mitigation parameters from at least one sensor comprised in the sensor device, or it may receive the measurement data from at least one other sensor device wirelessly directly from the at least one other sensor device or through the user interface device.

In an embodiment, the sensor device is configured to apply different frequency bands in the measurements for different sports types.

In an embodiment, the sensor device is a heart rate sensor configured to use a first frequency band when measuring a heart rate during a first sports type and to use a second frequency band when measuring the heart rate during a second sports type, wherein the first frequency band is different from the second frequency band, and wherein the first sports type is different from the second sports type.

Figure 7:
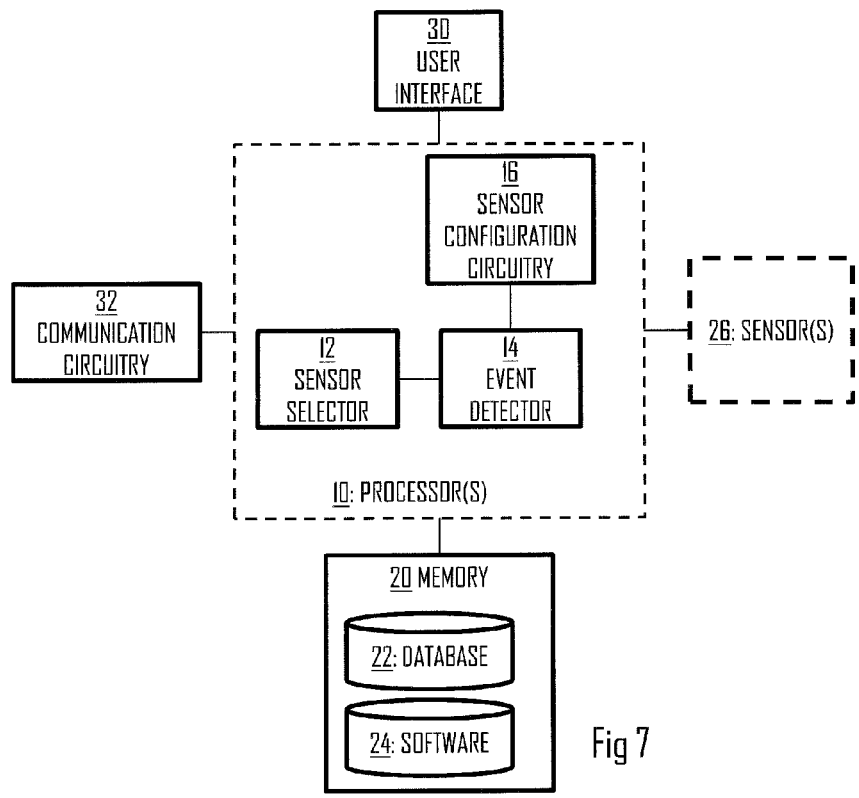
FIGS. 7 and 8 illustrate block diagrams of structures of apparatuses according to some embodiments of the invention.

FIG. 7 illustrates a block diagram of an apparatus according to an embodiment of the invention. The apparatus may be comprised in the above-described user interface device 104, 106, 110. The apparatus may comprise a user interface 30, as described above. The user interface may comprise at least a display and an input device. The apparatus may further comprise a communication circuitry 32 configured to provide the apparatus with wireless communication capability so that the apparatus may communicate wirelessly with sensor devices 102. The communication circuitry 32 may comprise well known wireless interface components such as one or more antennas, filters, amplifiers, frequency converters, etc. The apparatus may further comprise at least one internal sensor 26, wherein the internal sensor may also be included in the selection of the active set of sensors according to embodiments of the present invention. The internal sensor may be a heart rate sensor or a motion sensor, for example.

The apparatus may further comprise at least one processor 10. The processor(s) 10 may comprise an event detector circuitry 14 configured to process, in the measurement mode, measurement data received from at least one sensor device and to detect the predetermined event. Parameters or rules for detecting the predetermined event may be stored in a database 22 stored in a memory 20 of the apparatus. The database may store reference parameters for different sports types, for example, and the event detector circuitry 14 may be configured to determine whether or not the received measurement data matches with the reference parameters. If match is detected, the event associated with the matching reference parameters may be detected, and the event detector circuitry 14 may output the detected event to a sensor selector circuitry 12 and/or a sensor configuration circuitry 16. The sensor selector circuitry 12 may be configured to select the active set of sensors associated with the detected event. The database 22 may store active sets of sensors for each event and, thus, the sensor selector circuitry 12 may check from the database 22 which sensors need to be activated for the detected event and which currently active sensors are no longer needed. The sensor selector circuitry may thus control the communication circuitry 32 to transmit an appropriate reconfiguration message to the corresponding sensors, thus selecting the active set of sensors. The sensor configuration circuitry 16 may determine the measurement configuration for the currently active set of sensors. The database 22 may store measurement configurations for the sensors as associated with the events. The sensor configuration circuitry 16 may thus control the communication circuitry 32 to transmit in the reconfiguration message(s) the new measurement configurations to the (new) active set of sensors.

The memory 20 may additionally store one or more computer program products 24 defining the operation of the processor 10 and its circuitries 12 to 16. The circuitries 12 to 16 of the processor may thus be considered as different computer program modules executed by the same physical circuitries of the processor(s) 10.

Figure 8:
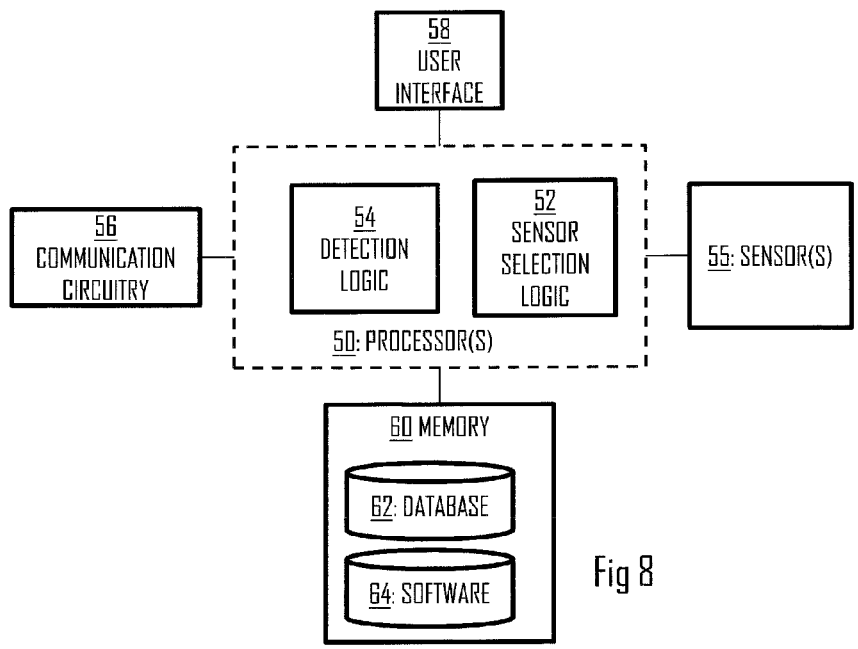

FIG. 8 illustrates a block diagram of an apparatus according to an embodiment of the invention. The apparatus of FIG. 8 may be comprised in the above-described sensor device 102. The apparatus may comprise a user interface 58 which may be simpler than the user interface of the user interface device, e.g. it may comprise a smaller display and/or less input options. The apparatus may further comprise a communication circuitry 32 configured to provide the apparatus with wireless communication capability so that the apparatus may communicate wirelessly with the user interface device and, optionally, with other sensor devices. The communication circuitry 32 may comprise well known wireless interface components such as one or more antennas, filters, amplifiers, frequency converters, etc. The apparatus comprises at least one internal sensor 55, in some embodiments multiple sensors 55, wherein the sensor(s) may be included in the selection of the active set of sensors according to embodiments of the present invention. The selection may apply to all sensors of the apparatus or to a subset of sensors of the apparatus. The sensor(s) 55 may comprise one or more of the above-described sensors.

The apparatus may further comprise at least one processor 50. The processor(s) 50 may comprise a sensor selection logic circuitry 52 configured to activate and deactivate the sensor(s) 55 according to reconfiguration messages received from the user interface device 104, 106, 110. The reconfiguration message may comprise, depending on the embodiment, various information elements enabling the sensor selection logic circuitry 52 to determine the active set of sensors amongst the sensor(s) 55, and a database 62 stored in a memory 60 of the apparatus may store mappings between the information elements comprised in the reconfiguration message and the active sets of sensors. As a consequence, the sensor selection logic circuitry 52 may read one or more of the information elements from the received reconfiguration message, check the database for an active set of sensors matching with the contents of the information elements, and output an activation signal or a deactivation signal to the sensor(s) 55 according to the result of the check. The processor(s) 50 may further comprise detection logic circuitry 54 carrying out the analysis of measurement signals received from the sensor(s) 55. The measurement signals may be converted into a digital form before they are input to the detection logic circuitry 54. The detection logic circuitry 54 may be configured to carry out analysis of the measurement signals according to the received reconfiguration messages. Table 1 above illustrates different procedures the detection logic circuitry may perform for the measurement signals: process according to a selected detection algorithm and associated parameters, select between data streaming and data storing modes, determine averaging window, etc. The reconfiguration message may carry at least one information element affecting the operation of the detection logic circuitry 54, and the database 62 may store mappings between the information elements and their actual effect on the detection logic circuitry 54. The detection logic circuitry 54 may thus extract the at least one information element from the received reconfiguration message, determine associated parameters by checking the database 62, and apply the determined parameters in the processing of the measurement signals.

The memory 60 may additionally store one or more computer program products 64 defining the operation of the processor 50 and its circuitries 52, 54. The circuitries 52, 54 of the processor 50 may thus be considered as different computer program modules executed by the same physical circuitries of the processor(s) 50.

In an embodiment, the apparatuses of FIGS. 7 and 8 are realized as one apparatus, and a communication link may be provided between the apparatus of FIG. 7 and the apparatus of FIG. 8. The communication link may be wired or wireless.

As used in this application, the term 'circuitry' refers to all of the following: (a) hardware-only circuit implementations, such as implementations in only analog and/or digital circuitry, and (b) to combinations of circuits and software (and/or firmware), such as (when applicable): (i) a combination of processor(s) or (ii) portions of processor(s)/software including digital signal processor(s), software, and memory (memories) that work together to cause an apparatus to perform various functions, and (c) to circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, a baseband integrated circuit or applications processor integrated circuit for a training computer or a sensor device.

It should be noted that while the Figures illustrate various embodiments of the sensor device and the user interface device, they are simplified block diagrams that only show some elements and functional entities, all being logical units whose implementation may differ from what is shown. The connections shown in these figures are logical connections; the actual physical connections may be different. Interfaces between the various elements may be implemented with suitable interface technologies. It is apparent to a person skilled in the art that the described devices may also comprise other functions and structures. It should be appreciated that details of some functions, structures, and elements, and the protocols used for communication are irrelevant to the actual invention. Therefore, they need not be discussed in more detail here, because such discussion might blur the invention with unnecessary details. The implementation and features of the devices according to the invention develop rapidly. Such development may require extra changes to the embodiments described above. Therefore, all words and expressions should be interpreted broadly and they are intended to illustrate, not to restrict, the embodiments. Although the devices have been depicted as separate single entities, different parts may be implemented in one or more physical or logical entities. It will be obvious to a person skilled in the art that, as technology advances, the inventive concept can be implemented in various ways. The invention and its embodiments are not limited to the examples described above but may vary within the scope of the claims.

What is claimed is:

1. An apparatus comprising:
at least one processor; and
at least one memory including a computer program code, wherein the at least one memory and the computer program code are configured, with the at least one processor, to cause the apparatus to perform operations comprising:
triggering a start of a physical exercise;
in response to said triggering, starting a measurement mode in which the apparatus receives measurement data of the physical exercise wirelessly from at least one sensor device and analyses the received measurement data;
detecting a predetermined event in the received measurement data during the physical exercise; and
in response to detecting said predetermined event, causing transmission of a reconfiguration message to at least one of the at least one sensor device to reconfigure at least one parameter associated with operation of said at least one of the at least one sensor device.

2. The apparatus of claim 1, wherein the predetermined event is detected in measurement data provided by a first sensor device of the at least one sensor device, and wherein the at least one memory and the computer program code are configured, with the at least one processor, to cause the apparatus to transmit the reconfiguration message to a second sensor device of the at least one sensor device.

3. The apparatus of claim 1, wherein the at least one memory and the computer program code are configured, with the at least one processor, to cause the apparatus to activate or deactivate at least one sensor of the at least one sensor device in response to the detection of the predetermined event.

4. The apparatus of claim 1, wherein the at least one memory and the computer program code are configured, with the at least one processor, to cause the apparatus to instruct, with the reconfiguration message, a change in an active set of sensors of the at least one sensor device for the physical exercise.

5. The apparatus of claim 1, wherein the at least one memory and the computer program code are configured, with the at least one processor, to cause the apparatus to detect the predetermined event in ambient measurement data during the physical exercise, wherein the ambient measurement data is not affected by activity of a user during the physical exercise.

6. The apparatus of claim 1, wherein a sensor device of the at least one sensor device is configured to determine interference mitigation parameters for the physical exercise, wherein different interference mitigation parameters are used for at least two different sports types, and to configure the sensor to apply the interference mitigation parameters in measurements performed by the sensor.

7. The apparatus of claim 6, wherein the sensor device is configured to apply different frequency bands in the measurements performed by the sensor for the at least two different sports types.

8. The apparatus of claim 6, wherein the sensor device is a heart rate sensor configured to use a first frequency band when measuring a heart rate during a first sports type and to use a second frequency band when measuring the heart rate during a second sports type, wherein the first frequency band is different from the second frequency band, and wherein the first sports type is different from the second sports type.

9. The apparatus of claim 6, wherein a wireless link is provided between the processor and the sensor device comprised in the apparatus.

10. An apparatus comprising:
at least one processor; and
at least one memory including a computer program code, wherein the at least one memory and the computer program code are configured, with the at least one processor, to cause the apparatus to perform operations comprising:
triggering a start of a physical exercise;
in response to said triggering, starting a measurement mode in which the apparatus receives measurement data of the physical exercise wirelessly from at least one sensor device and analyses the received measurement data;
detecting a change in a phase within a sports type of the physical exercise;
in response to detecting said change in the phase within the sports type, determining a new phase and a new set of sensors associated with the change in the phase within the sports type and causing the apparatus to transmit a reconfiguration message to at least one of the at least one sensor device to change to the new set of sensors.

11. An apparatus comprising:
at least one processor; and
at least one memory including a computer program code, wherein the at least one memory and the computer program code are configured, with the at least one processor, to cause the apparatus to perform operations comprising:
triggering a start of a physical exercise;
in response to said triggering, starting a measurement mode in which the apparatus receives measurement data of the physical exercise wirelessly from at least one sensor device and analyses the received measurement data;
detecting a change of a sports type from the received measurement data during the physical exercise; and
in response to detecting said change of the sports type, determining a new sports type from the received measurement data and a new set of sensors associated with the new sports type and causing transmission of a reconfiguration message to the at least one of the at least one sensor device to change to the new set of sensors.

12. An apparatus comprising:
at least one processor; and
at least one memory including a computer program code, wherein the at least one memory and the computer program code are configured, with the at least one processor, to cause the apparatus to perform operations comprising:
triggering a start of a physical exercise;
in response to said triggering, starting a measurement mode in which the apparatus receives heart rate measurement data of the physical exercise wirelessly from at least one heart rate sensor and analyses the received heart rate measurement data;
detecting a predetermined event in the heart rate measurement data;
reconfiguring operation of the at least one heart rate sensor to carry out at least one of the following in response to the detected predetermined event in the heart rate measurement data: change a wireless transmission mode of the heart rate measurement data, change a data storage mode of the heart rate measurement data in the at least one heart rate sensor.

13. The apparatus of claim 12, wherein if the wireless transmission mode is changed, changing the wireless transmission mode comprises at least one of the following: start or stop streaming the measurement data from the at least one heart rate sensor to the apparatus, trigger transmission of heart rate measurement data to the apparatus, change a communication protocol used between the at least one heart rate sensor and the apparatus, and change a security level of a connection between the at least one heart rate sensor and the apparatus.

14. The apparatus of claim 12, wherein if the data storage mode is changed, changing the data storage mode comprises at least one of the following: start or stop storing the measurement data in a memory of the at least one heart rate sensor, mark start or stop point for data to be stored permanently in the at least one heart rate sensor.

\* \* \* \* \*